(12) United States Patent
Srour et al.

(10) Patent No.: US 11,013,609 B2
(45) Date of Patent: May 25, 2021

(54) DEVICE FOR MAINTAINING AN INTERVERTEBRAL SPACE

(71) Applicant: SC MEDICA, Strasbourg (FR)

(72) Inventors: Robin Srour, Strasbourg (FR); Camille Srour, Strasbourg (FR)

(73) Assignee: SC MEDICA, Strasbourg (FR)

( * ) Notice: Subject to any disclaimer, the term of this patent is extended or adjusted under 35 U.S.C. 154(b) by 0 days.

(21) Appl. No.: 15/751,853

(22) PCT Filed: Aug. 11, 2016

(86) PCT No.: PCT/FR2016/052072
§ 371 (c)(1),
(2) Date: Feb. 10, 2018

(87) PCT Pub. No.: WO2017/025694
PCT Pub. Date: Feb. 16, 2017

(65) Prior Publication Data
US 2018/0228617 A1  Aug. 16, 2018

(30) Foreign Application Priority Data

Aug. 11, 2015 (FR) ...................... 15 57659
Dec. 17, 2015 (FR) ...................... 15 62563

(51) Int. Cl.
*A61F 2/44* (2006.01)
*A61F 2/46* (2006.01)
*A61F 2/30* (2006.01)

(52) U.S. Cl.
CPC ............ *A61F 2/442* (2013.01); *A61F 2/4611* (2013.01); *A61F 2/4603* (2013.01); *A61F 2002/302* (2013.01); *A61F 2002/30115* (2013.01); *A61F 2002/30125* (2013.01); *A61F 2002/30128* (2013.01); *A61F 2002/30243* (2013.01); *A61F 2002/30253* (2013.01);
(Continued)

(58) Field of Classification Search
CPC .... A61F 2/442; A61F 2/44; A61F 2002/4435; A61F 2002/444; A61F 2002/30113
See application file for complete search history.

(56) References Cited

U.S. PATENT DOCUMENTS 3,633,587 A * 1/1972 Hunt .................. A63H 5/00
606/235
5,059,193 A * 10/1991 Kuslich ................ A61F 2/4455
606/247
(Continued)

FOREIGN PATENT DOCUMENTS

EP        2058014 A1      5/2009
WO    2009143496 A1    11/2009
WO    2010147829 A1    12/2010

*Primary Examiner* — Ellen C Hammond
(74) *Attorney, Agent, or Firm* — Craft Chu PLLC; Andrew W. Chu

(57) ABSTRACT

The device for maintaining an intervertebral space is capable of being accommodated inside the disc, in place of the core. Natural anchoring is ensured by promoting the regrowth of fibre around at least part of the device. The possibility of ejection of the residual core is limited in order to avoid a renewed hernia, and mobility of the vertebral column is ensured. To this end, a subject of the invention is a device having at least two non-expansible concentric rings which between them form a free space and which are connected to each other via two junction summits.

3 Claims, 3 Drawing Sheets

(52) U.S. Cl.
CPC .............. *A61F 2002/30285* (2013.01); *A61F 2002/30593* (2013.01); *A61F 2002/30774* (2013.01); *A61F 2002/30785* (2013.01); *A61F 2002/30971* (2013.01); *A61F 2002/30985* (2013.01); *A61F 2002/444* (2013.01); *A61F 2002/4615* (2013.01); *A61F 2002/4627* (2013.01); *A61F 2002/4629* (2013.01); *A61F 2310/00023* (2013.01)

(56) References Cited

U.S. PATENT DOCUMENTS

| | | | | |
|---|---|---|---|---|
| 5,236,196 | A * | 8/1993 | Blankenburg | G09B 23/04 434/213 |
| 6,578,527 | B1 * | 6/2003 | Mathers | A01K 15/025 119/707 |
| 6,622,659 | B2 * | 9/2003 | Willinger | A01K 15/025 119/702 |
| 2002/0151979 | A1 * | 10/2002 | Lambrecht | A61B 17/70 623/17.16 |
| 2004/0211369 | A1 * | 10/2004 | Wechsler | A01K 15/025 119/707 |
| 2004/0249459 | A1 | 12/2004 | Ferree | |
| 2005/0234557 | A1 * | 10/2005 | Lambrecht | A61B 5/1076 623/17.16 |
| 2006/0057932 | A1 * | 3/2006 | Gick | A01K 15/025 446/269 |
| 2006/0067989 | A1 * | 3/2006 | Denesuk | A01K 15/026 424/442 |
| 2006/0162673 | A1 * | 7/2006 | Hurwitz | A01K 15/025 119/709 |
| 2007/0277747 | A1 * | 12/2007 | Gick | A01K 15/025 119/707 |
| 2008/0140203 | A1 * | 6/2008 | Davis | A61F 2/442 623/17.13 |
| 2010/0217335 | A1 | 8/2010 | Chirico | |
| 2011/0004308 | A1 * | 1/2011 | Marino | A61B 17/8811 623/17.12 |
| 2012/0100321 | A1 | 4/2012 | Goering | |
| 2015/0225087 | A1 | 8/2015 | Tanaka | |
| 2016/0015521 | A1 * | 1/2016 | Serrahima Tornel | A61F 2/442 623/17.16 |

* cited by examiner

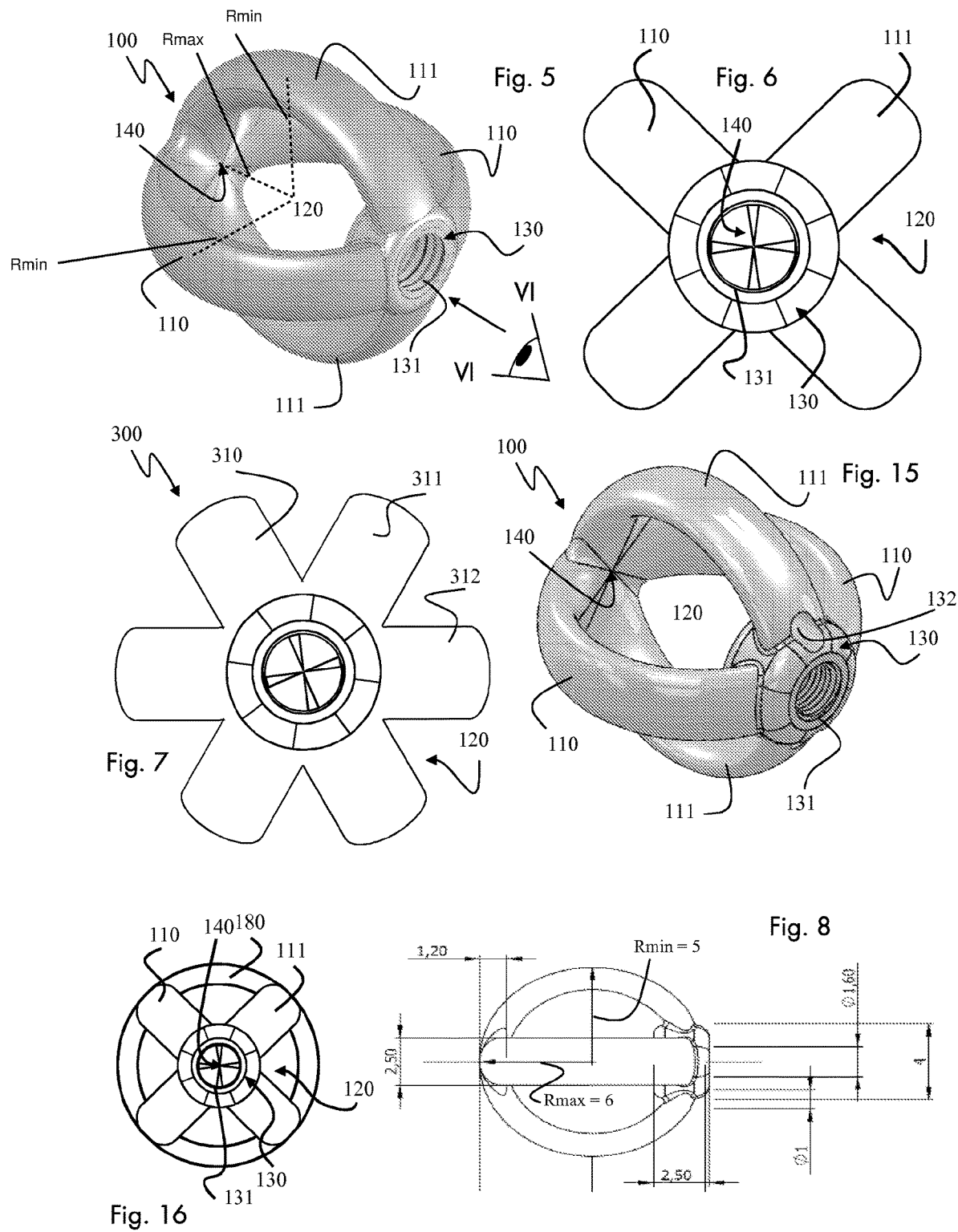

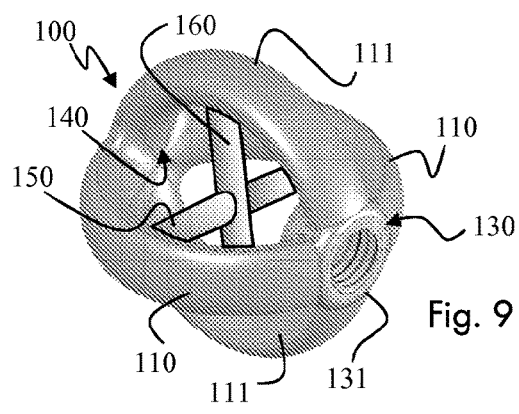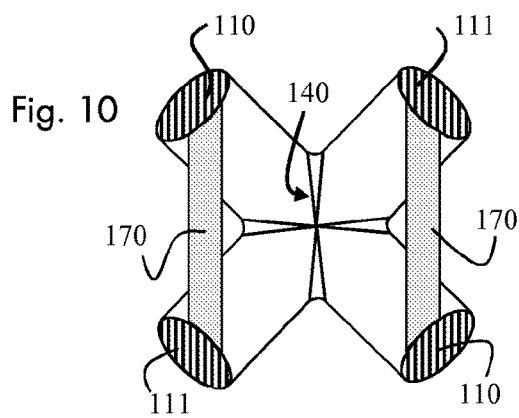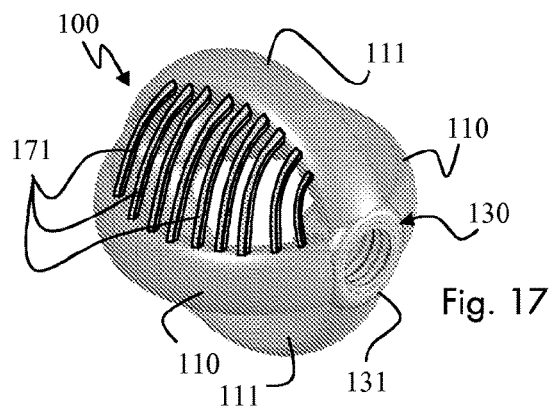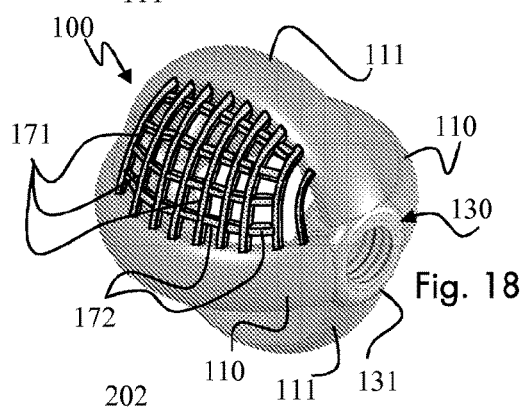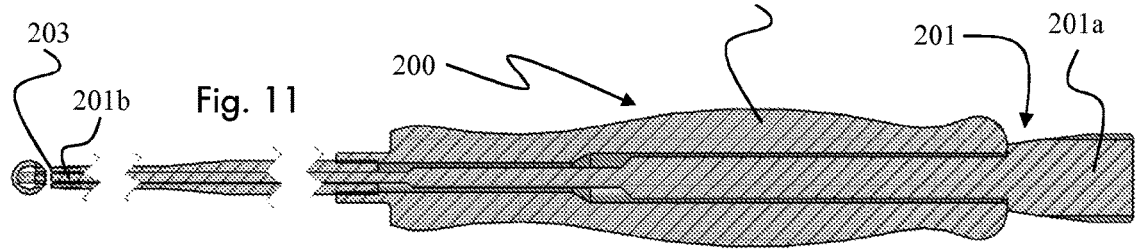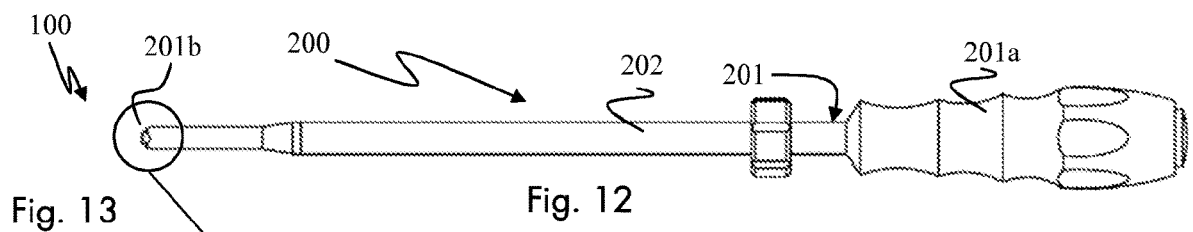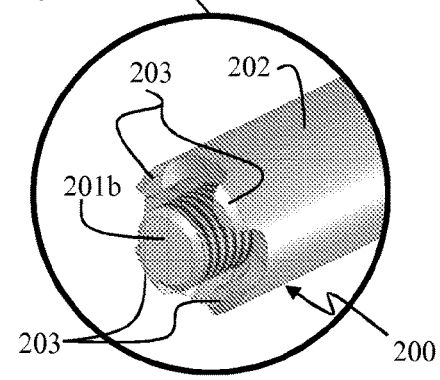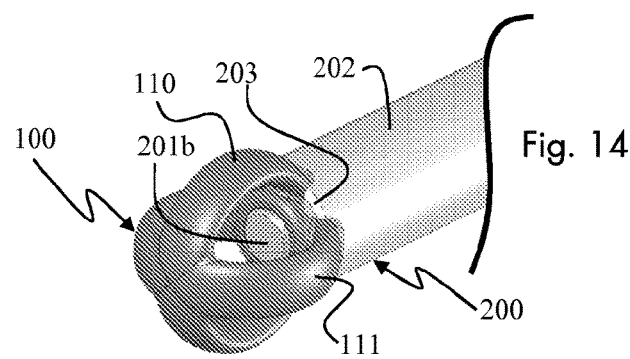

DEVICE FOR MAINTAINING AN INTERVERTEBRAL SPACE

CROSS-REFERENCE TO RELATED APPLICATIONS

The present application is a national phase application of the Patent Cooperation Treaty under 35 USC Section 371, which claims priority under 35 U.S.C. Section 119(b) and 35 CFR 1.55 from French Patent Application No. 15 57659, filed on 11 Aug. 2015 and French Patent Application No. 15 62563, filed on 17 Dec. 2015. See also Application Data Sheet.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

The invention relates to a device for manufacturing an intervertebral space intended to be inserted inside an intervertebral disc located between two adjacent vertebrae, in particular lumbar or cervical, in order to reestablish and maintain the intervertebral space after a discectomy, subsequent to a discopathy with or without discal hernia.

2. Description of Related Art Including Information Disclosed Under 37 CFR 1.97 and 37 CFR 1.98

An intervertebral disc is a fibrocartilage in the form of biconvex lenses inserted between the vertebrae. It is made up of a fibrous enclosure and a gelatinous core contained in the fibrous enclosure. The term discopathy is used in case of degeneration of the disc due to age, genetic factors, stresses imposed on the vertebral column, etc.

The term discal hernia is used when, following a crushing of the disc, part of the gelatinous core tears the fibrous enclosure and leaves the fibrous enclosure. The pain is primarily due to the fact that the core comes into contact with the adjacent nerves.

The treatment of the discal hernia is traditionally done as follows. After incision of the patient's skin, the surgeon surgically cuts the protruding part of the gelatinous core ("discectomy"), i.e., the part that leaves the disc. He also removes what he can of the rest of the core in the disc, to prevent it from leaving through the tear in the fibrous enclosure. However, part of the core still remains inaccessible and is a potential source of future hernia.

Next, he closes the incision in the patient's skin.

The reestablishment of the intervertebral space is not guaranteed. On the contrary, the removal of the core generally causes a decrease in the intervertebral space. Alternatively, when the disc is too destroyed, a much more burdensome operation must be considered: the near-complete removal of the disc and its replacement with an inter-somatic implant or inter-somatic cage (for example, Posterior Lumbar Interbody Fusion, or PLIF, technique, or Transforaminal Lumbar Interbody Fusion, or TLIF, technique). These inter-somatic cages are well known in the prior art, for example from document WO2005055869.

In general, they include a first part made up of four vertical walls with a commonplace shape, delimiting an open volume between them designed to receive a bone filler product, of the graft or bone substitute type, intended to come into contact with the cancellous bone of the vertebral plates to favor bone fusion between the two vertebrae. These inter-somatic cages are generally very stable, but the corollary to this stability is that they are highly resistant to the tensile and compression forces imposed on them by the vertebral column. Lastly, they cause fusion of the adjacent vertebrae, which no longer have any intervertebral mobility.

Document WO2010/147829 describes an intervertebral implant expandable between a substantially tubular position and a substantially spherical position.

This type of expandable implant does not make it possible to withstand very high intervertebral pressures, in particular at the lumbar vertebrae. This is due precisely to their expandable nature. Indeed, these devices must meet contradictory and incompatible requirements, namely being flexible enough to be able to be put in their final spherical shape manually by the physician, and rigid enough to withstand the intervertebral compression forces, from about 700 to 800 daN at the lumbar level.

Furthermore, this type of implant not having a high rigidity, it requires an insertion in the intervertebral space via a vertebra to be perforated, as shown by document WO2009/143496. This insertion through a minimally invasive/percutaneous route is highly traumatic, destroying the adjacent vertebra, which must repair itself gradually. This technique involves additional training and new skills to be acquired for the large majority of practitioners in question.

BRIEF SUMMARY OF THE INVENTION

The present invention makes it possible to treat discopathies, with or without discal hernia, through a largely atraumatic insertion route that is completely impossible to use with an expandable device.

The invention primarily aims to allow complementary treatment of discal hernias without removal of the intervertebral disc allowing a reestablishment and maintenance of the intervertebral space, decreased risks of recurrence (new ejection of the rest of the gelatinous core) and maintained freedom of movement of the column (forward flexion, backward extension, lateral incline, and rotation). In some surgical indications, it also makes it possible to replace the inter-somatic cages.

The aim of the invention is therefore to propose a device capable of being housed inside the disc, in place of the core, to ensure its natural anchoring (with no manual intervention by the surgeon, who cannot access the inside of the disc) while favoring fibrous regrowth around at least part of the device, limiting the possibility of ejection of the residual core to avoid a new hernia, and ensuring the mobility of the vertebral column.

The device according to the invention must make it possible to withstand static axial compression forces from modern medical tests (EC marking, for example) of at least 2000 daN, preferably at least 3000 daN, while allowing a simple and nontraumatic insertion protocol.

To that end, the invention relates to a device for maintaining an intervertebral space intended to be positioned inside an intervertebral disc, characterized in that it comprises at least two non-expandable concentric rings arranging a free space between them, and connected to one another by two junction summits. Non-expandable means that the device has only one configuration, its usage configuration, which gives it high mechanical rigidity and great solidity, without risk of collapse or rupture between two parts moving with respect to one another, like in expandable implants.

Regarding specific embodiments:

the rings can be elliptical and have a maximum radius and a minimum radius, the ratio between the maximum radius and the minimum radius being comprised between 1:1 and 1.5:1;

the rings can have an identical maximum radius and an identical minimum radius;

a reinforcing pillar can be positioned in a ring;

a reinforcing pillar can be positioned in each ring, preferably symmetrically relative to a center of the maintaining device;

a reinforcing pillar can be positioned between two rings;

two reinforcing pillars can be positioned each between two rings, preferably symmetrically relative to a center of the maintaining device;

a tapped orifice can be arranged at the center of a junction summit;

the device may further comprise a non-tapped orifice arranged in at least one ring, the tapped orifice and the non-tapped orifice having axes of revolution parallel to one another.

The invention also relates to a method for manufacturing a device for maintaining a preceding intervertebral space, consisting of aggregating biocompatible particles, preferably of titanium, layer by layer.

BRIEF DESCRIPTION OF THE SEVERAL VIEWS OF THE DRAWINGS

Other features of the invention will be set out in the description provided below, done in reference to the appended drawings.

FIG. 5 is a perspective schematic view of a first embodiment of a device for maintaining an intervertebral space according to the invention.

FIG. 6 is a schematic planar view of the embodiment of FIG. 5, seen facing the tapped orifice.

FIG. 7 is a schematic planar view of a second embodiment of a device for maintaining an intervertebral space according to the invention.

FIG. 8 is a schematic planar view with measurements of an example embodiment of a device for maintaining an intervertebral space according to the invention.

FIG. 9 is a perspective schematic view of a third embodiment of a device for maintaining an intervertebral space according to the invention, equipped with intra-ring reinforcements.

FIG. 10 is a sectional schematic view of a fourth embodiment of a device for maintaining an intervertebral space according to the invention, equipped with inter-ring reinforcements.

FIG. 11 is a sectional schematic view of a tool for positioning a device for maintaining an intervertebral space according to the invention.

FIG. 12 is a schematic planar side view of an alternative embodiment of a tool for positioning a device for maintaining an intervertebral space according to the invention.

FIG. 13 is a schematic perspective view of the fastening end of the positioning tool of FIG. 12.

FIG. 14 is a schematic perspective view of the fastening end of the positioning tool of FIG. 13, on which a device for maintaining an intervertebral space according to the invention is screwed.

FIG. 15 is a perspective schematic view of a fifth embodiment of a device for maintaining an intervertebral space according to the invention.

FIG. 16 is a sectional schematic view of a sixth embodiment of a device for maintaining an intervertebral space according to the invention, equipped with an annular reinforcement.

FIG. 17 is a schematic perspective view of a seventh embodiment of a device for maintaining an intervertebral space according to the invention, equipped with multiple inter-ring reinforcements.

FIG. 18 is a schematic perspective view of an eighth embodiment of a device for maintaining an intervertebral space according to the invention, equipped with multiple mesh inter-ring reinforcements.

DETAILED DESCRIPTION OF THE INVENTION

Figure 1:
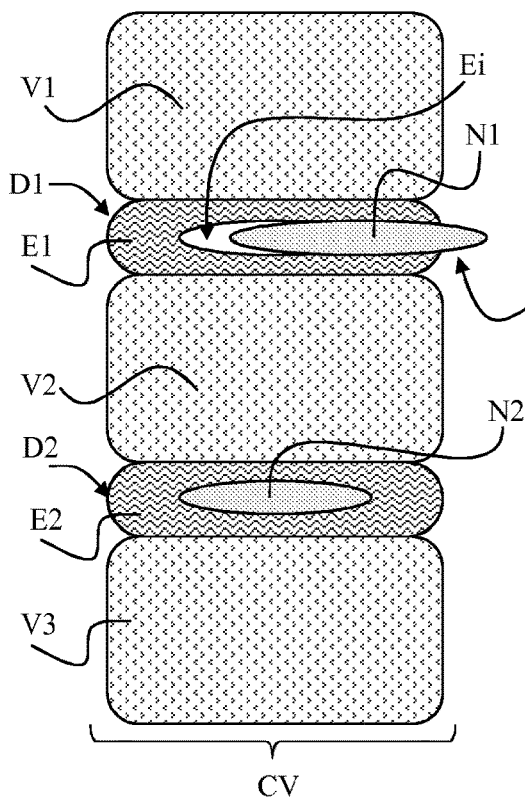
FIG. 1 is a schematic sectional view of a vertebral column portion having a discal hernia.
Figure 2:
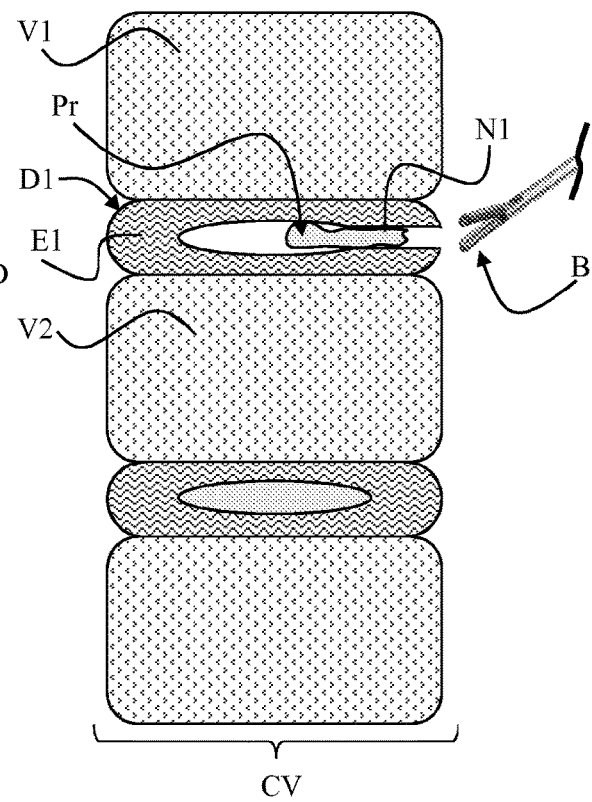
FIG. 2 is a schematic sectional view of the portion of the vertebral column of FIG. 1 after removal of part of the core.

FIGS. 1 and 2 illustrate the traditional steps of surgery for a discal hernia or discectomy. These same steps and the invention can also be used for a discopathy without associated discal hernia.

During the operation, the surgeon makes an incision in the patient's skin in order to access the disc D1 located between the vertebrae V1 and V2 of the vertebral column portion CV (FIG. 1). This disc D1 comprises a fibrous enclosure E1 and a gelatinous core N1 that has torn the enclosure E1 and is protruding, forming the discal hernia HD.

In comparison, the disc D2 located between the vertebrae V2 and V3 has a normal appearance, where the core N2 is confined in the intra-discal space E1, at the center of the enclosure E2.

Then, using a surgical cutting tool B (FIG. 2), of the scalpel and disc clamp type, the surgeon cuts the part of the core protruding from the disc, and cuts what he can of the rest of the core inside the opening in the disc (discectomy). A residual core portion Pr then remains.

This traditional discal hernia discectomy technique, called "open", is the most widely practiced spinal operation (22% of the 152,372 spinal operations done in France in 2013, according to the Agence technique de l'information sur l'hospitalisation).

Owing to the invention, the surgeon can reestablish and maintain the intervertebral space during this traditional operation, directly after removing the discal hernia, without having to perforate an adjacent vertebra, or turn the patient over.

Figure 3:
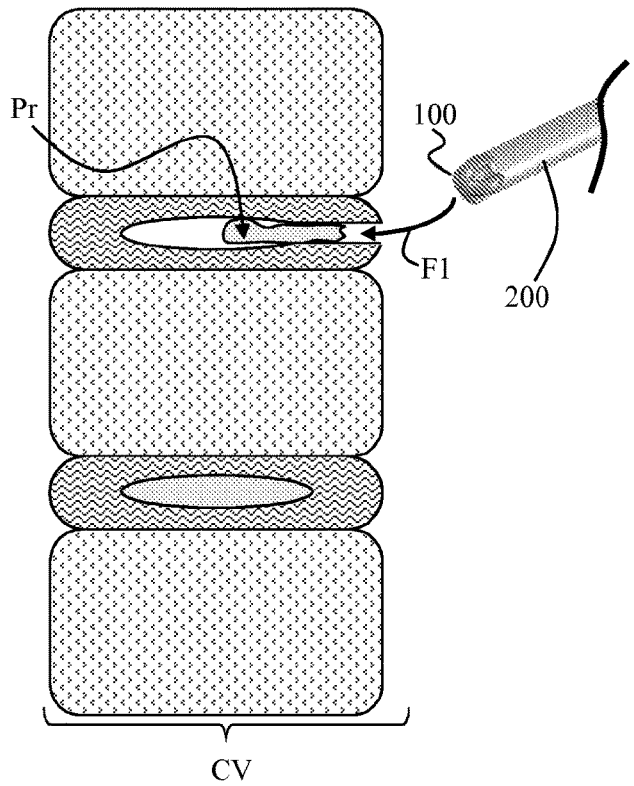
FIG. 3 is a schematic sectional view of the vertebral column portion of FIG. 2, in which a device for maintaining an intervertebral space according to the invention is being positioned.

To that end, the surgeon forcibly inserts, directly in the intervertebral space via the orifice created by the discal hernia (FIG. 3), a device 100 for maintaining an intervertebral space according to the invention, while providing hammer blows on the outer end of an implant-holder tool 200, which will be described in more detail in relation to FIGS. 11 to 14.

The physician will have placed and removed test implants (called "ghost implants") beforehand with different diameters to prepare the niche and determine the appropriate size for the patient of the device for maintaining an intervertebral space according to the invention.

Figure 4:
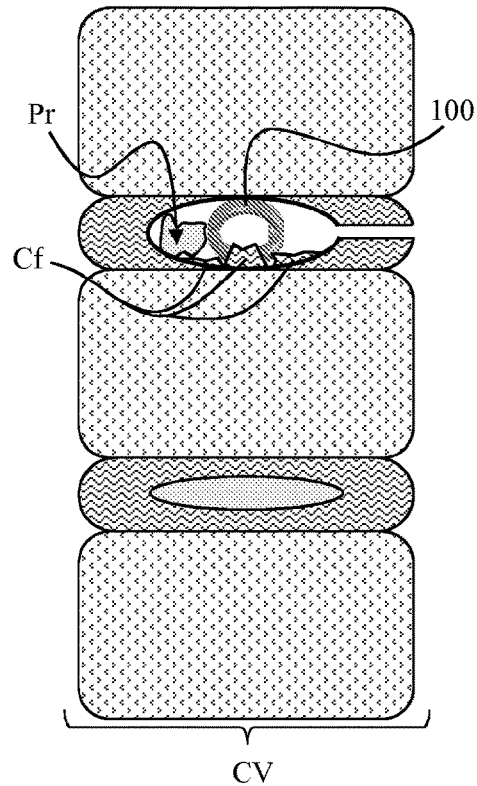
FIG. 4 is a schematic sectional view of the vertebral column portion of FIG. 3, in which a device for maintaining an intervertebral space according to the invention is in the usage position.

The insertion along arrow F1 is done in the torn part of the enclosure of the disc, which pushes back the residual core portion Pr toward the inside of the intra-discal space (FIG. 4).

As will be explained in more detail below, the device 100 according to the invention also allows an easy insertion owing to its elliptical outer shape, preferably spherical. Furthermore, the use of rings to make up the device 100 makes it possible to free a significant passage for the tissues of the enclosure, participating in the ease of insertion, and allows colonization of fiber cells Cf, participating in the natural anchoring of the device according to the invention.

A first embodiment of a device for maintaining an intervertebral space according to the invention is illustrated in FIG. 5. The device 100 comprises, in this example, two non-expandable, concentric rings 110 and 111 with identical radii Rmin and identical radii Rmax. The first concentric ring 110 has a first proximal end 110A and a first distal end 110B opposite the first proximal end. The second concentric ring 111 having a second proximal end 111A and a second distal end 111B opposite the second proximal end. In other words, the rings are identical and concentric. They are connected to one another by two junction summits 130 and 140, arranging a free space 120 between them. The distal junction summit 140 is comprised of the first distal end and the second distal end. The proximal junction summit 130 is comprised of the first proximal end and the second proximal end.

In the embodiment illustrated in FIG. 8, the rings are elliptical and have a maximum radius Rmax and a minimum radius Rmin, the ratio between the maximum radius Rmax and the minimum radius Rmin being comprised between 1:1 and 1.5:1.

In the embodiment illustrated in FIG. 5, the rings are circular and have an identical maximum radius Rmax and minimum radius Rmin, the ratio between the maximum radius Rmax and the minimum radius Rmin being equal to 1:1.

For information and non-limitingly, in the considered application, Rmin is comprised between 2 and 7 mm, the smallest sizes generally being reserved for cervical vertebrae and the largest sizes for lumbar vertebrae.

They have a section such that the contact surface between the rings and the tissues of the patient is rounded toward the outside of the device according to the invention.

A tapped orifice 131 is arranged at the center of the proximal junction summit 130. The tapped orifice 131 has threads 131A and is positioned at a center of the proximal junction summit facing away from the distal junction summit. The tapped orifice has an axis of revolution 131B, and the first concentric ring and the second concentric ring are rotatable around the axis of revolution. It allows the fastening to the positioning tool 200 (see FIGS. 11 to 14), which includes a knob 201 provided with a gripping end 201a and a threaded end 201b intended to be screwed into the tapped orifice 131, the knob 201 being mounted rotating in a handle 202.

In order to allow the unscrewing of the positioning tool 200 without rotating the device for maintaining an intervertebral space according to the invention, the handle 202 of the positioning tool includes at least two pilot points 203, preferably four pilot points 203 (see FIG. 13), intended and configured to be inserted between two rings 110-111 (see FIG. 14). Alternatively, it is possible to provide at least one non-tapped orifice arranged in at least one of the rings 110-111, and intended to receive a locking pilot point 203 supported by the positioning tool. The tapped orifice 131 and the non-tapped orifice(s) 132 have axes of revolution parallel to one another.

In FIG. 15, two non-tapped orifices 132 are provided arranged in the ring 111, on either side of the tapped orifice 131, and intended to receive two blocking pilot points 203 supported by the positioning tool.

The threaded knob makes it possible to fasten the device according to the invention on the positioning tool 200, and the pilot points 203 make it possible to keep the device in position and prevent it from rotating with the knob. It is thus possible to cause the device to enter inside the disc while applying small oscillating movements or tapping on it with a hammer, without risk of unscrewing the device from the positioning tool. The tool is further comprised of a plurality of pilot points 203 being radially arranged around the knob 201 and alternating between the first proximal end 110A of the first concentric ring 110 and the second proximal end 111A of the second concentric ring 111. The pilot points are in removable engagement around the proximal junction summit and between the first and second concentric rings 110, 111 so as to lock the knob to the tapped orifice for placement in an orientation and so as to hold the first and second concentric rings in that orientation, while the knob 201 is unscrewed from the tapped orifice. The pilot points 203 are in removable engagement from the first and second concentric rings 110, 111 so as to release the entire positioning tool 200 from the device 100 in the orientation of the placement. The pilot points 203 prevent unscrewing.

When the surgeon feels that the device is in the correct position, he unscrews the knob 201. The device 100 is then only fastened to the handle by the pilot points 203 (blocked between two rings or in the non-tapped orifices 132), such that the surgeon needs only delicately remove the tool 200, leaving the device 100 according to the invention in the usage position, inside the intervertebral disc.

The structure in concentric rings has many advantages. First of all, it makes it possible to free a space 120 between the rings, which facilitates the insertion of the device by allowing the tissue to deform toward the inside of the device.

Furthermore, this space 120 between the rings 110-111 allows rapid colonization by the fibrous tissues from the enclosure. The device can therefore be anchored naturally and relatively quickly. Alternatively, or in combination, it may be provided to inject an anchoring product (such as glue, cement or bone graft) or a product favoring cell development through the orifice 130. Any other product that could be necessary for operation may also be injected.

In this case, it is advantageously provided, according to the invention, that the threaded knob 201 of the positioning tool 200 includes a central channel connected to a product reservoir (not shown). The product can then be injected before unscrewing the knob 201.

The structure in non-expandable concentric rings also makes it possible to push back the residual core owing to the junction summit 140 opposite the junction summit 130.

The device according to the invention thus makes it possible to limit the risks of the residual core coming out by pushing it back and maintaining a low enough intra-discal pressure to prevent the expulsion of the residual core. It makes it possible to maintain the discal height, decrease the pressure on the residual disc and thus avoid hernia recurrences. It also makes it possible to preserve the adjacent vertebral stages.

The structure in non-expandable concentric rings also makes it possible to ensure optimal mobility of the vertebral column, which may still pivot owing to the elliptical device 100 (preferably spherical) according to the invention while benefiting from the natural mechanical properties of the enclosure of the disc, which remains in place. To that end, the ratio between the maximum radius Rmax and the minimum radius Rmin is smaller than 1.5:1, preferably equal to 1:1. In other words, it is possible to manufacture a device according to the invention that is slightly ovoid, for example to increase the contact surface with the patient's body, but it is necessary to limit the length to one and one half times the height.

With an expandable device, it would be impossible to use the insertion route according to the invention: one would insert, then open the device. This opening would be impossible manually without easing the vertebrae. To counter the intervertebral pressure, it would therefore be necessary to use spacers, which prohibitively increases the risk of additional trauma and operating complications. Owing to the non-expandable structure of the device according to the invention, forcible insertion is possible. The spherical/elliptical shape prevents any risk of trauma during this insertion, while making it possible to separate the vertebrae just enough to place the implant correctly. There is therefore no risk of over-separating the vertebrae.

Lastly, the structure in concentric rings makes it possible to obtain good stability of the device owing to fibrous regrowth, which will colonize this device, while limiting the contact zones with the patient's tissue owing to the rounded summits of the rings according to the invention. The risks of destroying these tissues are therefore limited.

In one alternative embodiment, illustrated in FIG. 7, the device 300 according to the invention includes more than two rings: it includes three concentric rings 310, 311 and 312. The other features remain identical.

Increasing the number of rings may allow better control during the positioning of the device and better control of the mobility of the column after operation.

Nevertheless, by increasing the number of rings, one increases the cost of the implant and limits the space between the rings. It is consequently appropriate to adapt the number of rings and their section so that the space between the rings allows good colonization of the fibrous cells. In practice, one will preferably ensure that the free space 120 between the rings is at least 30 mm$^3$, while retaining a spherical or near-spherical structure (when the ratio between the maximum radius Rmax and the minimum radius Rmin is greater than 1:1 and less than or equal to 1.5:1), Rmin being comprised between 2 and 7 mm.

The device according to the invention is therefore compact while offering significant inner space, allowing good colonization of the fibrous cells. Owing to this non-expandable structure, it may therefore be easily inserted and anchored naturally (by fibrous regrowth) in the body. The device 100-300 according to the invention for maintaining an intervertebral space is advantageously obtained by additive manufacturing by layers. Thus, it is manufactured by aggregating particles, layer by layer, preferably of titanium due to its solidity and biocompatibility.

This section and the material of the rings are chosen to allow the device according to the invention to withstand static axial compression forces of at least 2000 daN, preferably at least 3000 daN, while respecting the optimal intervertebral dimensions, which is possible owing to the non-expendable nature of the device according to the invention. The term withstand means that the device according to the invention must not be crushed or broken when it experiences a static axial compression force of at least 2000 daN, preferably of at least 3000 daN.

For example, an implant according to the invention is made from titanium, and it has a general diameter comprised between 7.5 and 14 mm. Each ring has a substantially circular or elliptical cross-section between 1.2 and 2.5 mm in diameter.

An expandable device may not be configured for such strength, at the risk of not being able to be deployed.

The layer-by-layer aggregation method is advantageously carried out by a three-dimensional printer.

To ensure the rigidity of the device, it is advantageously possible to provide inner reinforcements, located within the device.

FIG. 9 illustrates an embodiment in which a reinforcing pillar 150-160 is positioned in each ring, preferably symmetrically relative to a center of the maintaining device (made up of the barycenter of the sphere or ovoid). In other words, in this embodiment, the device includes intra-annular reinforcements, each reinforcing pillar being in contact with two diametrically opposite parts of a same ring. FIG. 10 illustrates an embodiment in which a reinforcing pillar 170 is positioned between two rings 110-111.

Preferably, at least two reinforcing pillars 170 are positioned between two rings 110-111, preferably symmetrically relative to the center of the maintaining device. In other words, in this embodiment, the device includes inter-annular reinforcements, each reinforcing pillar being in contact with two parts of two different rings 110-111.

FIG. 16 illustrates one particular embodiment of FIG. 10, in which a reinforcing pillar 180 is positioned perpendicular to the rings 110-111. Advantageously, this reinforcing pillar 180 is made up of a reinforcing ring positioned perpendicular to the rings 110-111.

Of course, a device for maintaining the intervertebral space according to the invention may comprise a combination of the reinforcing means illustrated in FIGS. 9, 10 and 16.

Thus, for example, FIG. 17 illustrates an embodiment in which the device for maintaining the intervertebral space includes a plurality of pillars 171 arranged next to one another (parallel or radially) and in contact with two halves of two different rings 110-111. In this figure, only one quarter of the device for maintaining the intervertebral space according to the invention is illustrated as being provided with pillars 171. Of course, in reality, all of the inter-annular spaces are equipped with such pillars 171 in this embodiment.

This plurality of pillars 171 makes it possible to distribute the support for the rings while making it possible to provide narrow pillars 171, leaving space for cell colonization.

According to another embodiment illustrated in FIG. 18, the reinforcing pillars 171 are further connected to one another by junction portions 172 in order to form a reinforcing mesh 171-172 positioned between two halves of two different rings 110-111. In this figure, only one quarter of the device for maintaining the intervertebral space according to the invention is illustrated as being provided with pillars 171 and junction portions 172. Of course, in reality, all of the inter-annular spaces are equipped with such pillars 171 and such junction portions 172 in this embodiment.

The reinforcing mesh 171-172 not only makes it possible to stiffen the device for maintaining the intervertebral space according to the invention, but also decreases the risk of the device being pushed into the vertebral plates.

The space between the pillars 171 and the junction portions 172 must nevertheless be maximized to ensure good cell colonization. Maximizing these spaces is made possible by the great rigidity of the much thicker rings.

Lastly, the device for maintaining the intervertebral space according to the invention includes very solid and rigid regions, which are the rings 110 and 111, and reinforcing regions made up of thinner pillars 171 and junction portions 172 that make it possible to limit the risks of sinking into the vertebral plates. In other words, the device for maintaining the intervertebral space according to the invention is a sphere or a heterogeneous ovoid, with non-expandable, thick and rigid parts, which are the rings 110-111, and thinner non-expandable parts, which are pillars 171 or mesh 171-172, making it possible to distribute the load over the vertebral plates.

The invention therefore allows complementary treatment of discal hernias, or even hernia-free discopathies, without removal of the intervertebral disc allowing a reestablishment and maintenance of the intervertebral space, decreased risks of recurrence (new ejection of the rest of the gelatinous core), and maintained freedom of movement of the column.

The device according to the invention is housed easily inside the disc, in place of the core, and allows natural anchoring while favoring fibrous regrowth around the rings.

We claim:

1. A system for maintaining an intervertebral space, the system comprising:
    a device for maintaining an intervertebral space, the device comprising:
        a first concentric ring having a first proximal end and a first distal end opposite said first proximal end;
        a second concentric ring having a second proximal end and a second distal end opposite said second proximal end;
        a distal junction summit being comprised of said first distal end and said second distal end;
        a proximal junction summit being comprised of said first proximal end and said second proximal end; and
        a tapped orifice having threads and being positioned at a center of said proximal junction summit facing away from said distal junction summit and having an axis of revolution, said first concentric ring and said second concentric ring being rotatable around said axis of revolution; and
    a tool having a gripping end and a threaded end opposite said gripping end and being comprised of:
        a handle at said gripping end;
        a knob at said threaded end; and
        a plurality of pilot points radially arranged around said knob, said pilot points being in removable engagement with said proximal junction summit and alternating between said first concentric ring and said second concentric ring,
    wherein said knob is in removable threaded engagement with said threads of said tapped orifice.

2. The system for maintaining, according to claim 1, wherein said plurality of pilot points is in removable engagement with said proximal junction summit, and wherein said pilot points alternate between said first proximal end of said first concentric ring and said second proximal end of said second concentric ring so as to hold the device when the knob is removed from said proximal junction summit.

3. The system for maintaining, according to claim 1, wherein said pilot points are in removable engagement around said proximal junction summit so as to release said tool from the device.

* * * * *